United States Patent
Guo et al.

(10) Patent No.: US 11,521,073 B2
(45) Date of Patent: Dec. 6, 2022

(54) METHOD AND SYSTEM FOR HYPERSPECTRAL INVERSION OF PHOSPHORUS CONTENT OF RUBBER TREE LEAVES

(71) Applicants: Rubber Research Institute, Chinese Academy of Tropical Agricultural Sciences, Haikou (CN); Institute of Scientific And Technical Information, Chinese Academy of Tropical Agricultural Sciences, Haikou (CN)

(72) Inventors: Pengtao Guo, Haikou (CN); Maofen Li, Haikou (CN); Zhengzao Cha, Haikou (CN); Hongzhu Yang, Haikou (CN); Meirong Bei, Haikou (CN); Peisong Zhang, Haikou (CN); Wei Luo, Haikou (CN); Wei Yao, Haikou (CN)

(73) Assignees: RUBBER RESEARCH INSTITUTE, CHINESE ACADEMY OF TROPICAL AGRICULTURAL SCIENCES, Hainan (CN); INSTITUTE OF SCIENTIFIC AND TECHNICAL INFORMATION, CHINESE ACADEMY OF TROPICAL AGRICULTURAL SCIENCES, Hainan (CN)

(*) Notice: Subject to any disclaimer, the term of this patent is extended or adjusted under 35 U.S.C. 154(b) by 375 days.

(21) Appl. No.: 16/837,175

(22) Filed: Apr. 1, 2020

(65) Prior Publication Data
US 2021/0056424 A1 Feb. 25, 2021

(30) Foreign Application Priority Data
Aug. 20, 2019 (CN) .......................... 201910766841.6

(51) Int. Cl.
*G01N 21/31* (2006.01)
*G06N 3/08* (2006.01)
(Continued)

(52) U.S. Cl.
CPC ............. *G06N 3/084* (2013.01); *G01N 21/31* (2013.01); *G01N 33/0098* (2013.01); *G06K 9/6257* (2013.01)

(58) Field of Classification Search
CPC .......... G06N 3/02; G06N 3/086; G01N 21/31; G01J 3/2823; G01J 2003/2826
See application file for complete search history.

(56) References Cited

PUBLICATIONS

Hayder Hasan, "A Comparison Between Support Vector Machine (SVM) and Convolutional Neural Network (CNN) Models For Hyperspectral Image Classification", 2019 (Year: 2019).*

(Continued)

*Primary Examiner* — Maurice C Smith
(74) *Attorney, Agent, or Firm* — Tarolli, Sundheim, Covell & Tummino LLP (57) ABSTRACT

A method is provided for hyperspectral inversion of a phosphorus content of rubber tree leaves. The method includes: acquiring hyperspectral data of to-be-detected rubber tree leaves; extracting key wavelengths of the rubber tree leaves according to the hyperspectral data and a pre-established wavelength extraction model, where the key wavelengths are related to the phosphorus content of the rubber tree leaves, and the pre-established wavelength extraction model is obtained by learning and training hyperspectral sample data and sample phosphorus content data pairs in a pre-established sample database by adopting a competitive adaptive reweighted sampling (CARS) algorithm and a successive projection algorithm (SPA); and inputting the key wavelengths into a pre-established phosphorus content prediction model to calculate the phosphorus content of the to-be-detected rubber tree leaves. Moreover, the CARS (Continued)

algorithm and the SPA are comprehensively applied to extract the key wavelengths closely related to the phosphorus content of the rubber tree leaves.

20 Claims, 6 Drawing Sheets

(51) Int. Cl.
    *G01N 33/00*     (2006.01)
    *G06K 9/62*     (2022.01)

(56) References Cited

PUBLICATIONS

Xiaohui Lua, "Identification of authenticity, quality and origin of saffron using hyperspectral imaging and multivariate spectral analysis", Nov. 12, 2019 (Year: 2019).*

Pent-Tao Guo, "A robust method to estimate foliar phosphorus of rubber trees with hyperspectral reflectance" Oct. 5, 2018 (Year: 2018).*

Guo Pengtao, "Prediction of leaf phosphorus contents for rubber seedlings based on hyperspectral sensitive bands and back propagation artificial neural network" Jan. 2016 (Year: 2016).*

Yue Xuejun, "Prediction model of phosphorus content for citrus leaves during different growth periods based on hyperspectrum", Apr. 2015 (Year: 2015).*

Pengtao, et al. "Prediction of leaf phosphorus contents for rubber seedlings based on hyperspectrai sensitive bands and back propagation artificial neural network", Rubber Research Institute, Chinese Academy of Tropical Agriculture Science, Danzhou 571737, China.

Zhang Yakun, "Research on Detection Method of Soybean Nutrient Based on Multiscale Hyperspectrai Imaging Technology", Harbin China Dec. 2018.

Wei, et al. "Using CARS-SPA algorithm combined with hyperspectral to determine reducing sugars content in potatoes", 1. School of Electrical and Information, Northeast Agricultural University, Harbin 150030, China; 2. Department of Computer, Harbin Finance University, Harbin 150030, China, Feb. 2016.

Chinese Office Action for Application No. 201910766841.6 dated Mar. 2, 2020. No English Translation Available.

\* cited by examiner

METHOD AND SYSTEM FOR HYPERSPECTRAL INVERSION OF PHOSPHORUS CONTENT OF RUBBER TREE LEAVES

RELATED APPLICATIONS

The present invention is a Nonprovisional Application under 35 USC 111(a), claiming priority to Serial No. CN 201910766841.6, filed on 20 Aug. 2019, the entirety of which is incorporated herein by reference.

TECHNICAL FIELD

The present application relates to the technical field of hyperspectral inversion, and in particular, to a method and system for hyperspectral inversion of a phosphorus content of rubber tree leaves, a computer device and a storage medium.

BACKGROUND

Natural rubber is an important strategic material and industrial raw material. Nutritional conditions of rubber trees are directly related to natural rubber yield and quality, years of production of rubber trees, etc. Phosphorus is an indispensable nutrient element for plant growth and development. It participates in the metabolic process of substances in plants in various ways, plays a vital role in respiratory metabolism, sugar metabolism, enzymatic reaction, hormone metabolism, etc., and serves for healthy growth of crops. Therefore, it is very important to study the phosphorus content of rubber tree leaves.

At present, in researches on the phosphorus content, full spectrum information is usually used as an explanatory variable and partial least squares regression (PLSR) is used to construct a model for hyperspectral inversion of a phosphorus content of plant leaves. Hyperspectral data has hundreds of pieces of spectral information, the number of which is often much greater than that of samples of target variables, and there is information redundancy between these spectra. The PLSR can compress these hundreds of pieces of spectral information into several unrelated principal components, and these principal components are used as explanatory variables to build a model, thus solving the problem of high dimension of data and information redundancy in hyperspectral data modeling. However, this method still has some defects. First of all, there is inevitably some noise information or information unrelated to target variables in hyperspectral data. The information is included in the compressed principal components. Taking these principal components as input, the real relationship between the target variables and the principal components is distorted, thus reducing prediction accuracy of the model. In addition, PLSR can only fit the linear relationship between the explanatory variables and the target variables, and cannot fit the nonlinear relationship. However, there is often a nonlinear relationship between spectral information and the phosphorus content of plant leaves. Therefore, the PLSR cannot fully capture the relationship between the spectral information and the phosphorus content of plant leaves, resulting in low prediction accuracy of the model.

SUMMARY

In view of this, it is necessary to provide a method and system for hyperspectral inversion of a phosphorus content of rubber tree leaves, a computer device and a storage medium to solve the foregoing technical problems.

A method for hyperspectral inversion of a phosphorus content of rubber tree leaves includes:

acquiring hyperspectral data of to-be-detected rubber tree leaves;

extracting key wavelengths of the rubber tree leaves according to the hyperspectral data and a pre-established wavelength extraction model, where the key wavelengths are related to the phosphorus content of the rubber tree leaves, and the pre-established wavelength extraction model is obtained by learning and training hyperspectral sample data and sample phosphorus content data pairs in a pre-established sample database by adopting a competitive adaptive reweighted sampling (CARS) algorithm and a successive projection algorithm (SPA); and inputting the key wavelengths into the pre-established phosphorus content prediction model to calculate the phosphorus content of the to-be-detected rubber tree leaves, where the pre-established phosphorus content prediction model is obtained by learning and training key sample wavelengths and the sample phosphorus content data by adopting a back-propagation neural network (BPNN) algorithm, and the key sample wavelengths are obtained by inputting the hyperspectral data in the sample database into the pre-established wavelength extraction model.

In an embodiment, before the step of acquiring hyperspectral data of to-be-detected rubber tree leaves, the method includes:

collecting to-be-detected rubber tree leaves;

performing spectral measurement on the to-be-detected rubber tree leaves by using a spectrometer tester to obtain original hyperspectral data of the to-be-detected rubber tree leaves; and denoising the original hyperspectral data to obtain hyperspectral data.

In an embodiment, a method for establishing a pre-established sample database includes:

collecting a plurality of rubber tree leaf samples from rubber trees on different soil parent materials in a sample collection area within a preset sample collection time;

removing impurities on the surface of each rubber tree leaf sample; performing spectral measurement on each rubber tree leaf sample after impurity removal by using a spectrometer to obtain original hyperspectral data of each sample;

adopting a filter function to denoise the original hyperspectral data of each sample to obtain denoised hyperspectral sample data;

detecting a phosphorus content of each rubber tree leaf sample to obtain phosphorus content data of each sample, where the sample phosphorus content data corresponds to the hyperspectral sample data; and establishing the sample database according to the denoised hyperspectral sample data and the sample phosphorus content data.

In an embodiment, a method for establishing a pre-established wavelength extraction model includes:

dividing the hyperspectral sample data and the sample phosphorus content data of the sample database into a training set and a test set according to a preset dividing ratio;

selecting hyperspectral data sample and sample phosphorus content data in a preset extraction ratio from the training set as input variables to learn and train the CARS algorithm and the SPA, and determining key parameters of the CARS algorithm and the SPA; and determining the wavelength extraction model according to the key parameters of the CARS algorithm and the SPA.

In an embodiment, a method for establishing the pre-established phosphorus content prediction model includes:

inputting the hyperspectral sample data in the test set into the pre-established wavelength extraction model to obtain key wavelengths of the samples;

taking the key sample wavelengths and the sample phosphorus content data corresponding to the key sample wavelengths as input variables to learn and train the BPNN algorithm, and determining key parameters of the BPNN algorithm; and determining the phosphorus content prediction model according to the key parameters of the BPNN algorithm.

In an embodiment, the step of adopting a filter function to denoise the original hyperspectral data of each sample to obtain denoised hyperspectral sample data includes:

adopting butter and filtfilt functions to denoise the original hyperspectral data of each sample.

In an embodiment, the step of dividing the hyperspectral sample data and the sample phosphorus content data of the sample database into a training set and a test set according to a preset dividing ratio includes:

adopting a Kennard-Stone algorithm to divide the hyperspectral sample data and the sample phosphorus content data of the sample database into a training set and a test set, where the ratio of the data volume of the training set to the data volume of the test set is 2:1.

A system for hyperspectral inversion of a phosphorus content of rubber tree leaves includes:

a hyperspectral data acquisition module, configured to acquire hyperspectral data of to-be-detected rubber tree leaves;

a key wavelength extraction module, configured to extract key wavelengths of the rubber tree leaves according to the hyperspectral data and a pre-established wavelength extraction model, where the key wavelengths are related to the phosphorus content of the rubber tree leaves, and the pre-established wavelength extraction model is obtained by learning and training hyperspectral sample data and sample phosphorus content data pairs in a pre-established sample database by adopting a CARS algorithm and an SPA; and a phosphorus content calculation module, configured to input the key wavelengths into the pre-established phosphorus content prediction model to calculate the phosphorus content of the to-be-detected rubber tree leaves, where the pre-established phosphorus content prediction model is obtained by learning and training key sample wavelengths and the sample phosphorus content data by adopting a BPNN algorithm, and the key sample wavelengths are obtained by inputting the hyperspectral data in the sample database into the pre-established wavelength extraction model.

A computer device includes a memory, a processor, and a computer program stored in the memory and executable on the processor, where when the computer program is executed by the processor, the following steps are implemented:

acquiring hyperspectral data of to-be-detected rubber tree leaves;

extracting key wavelengths of the rubber tree leaves according to the hyperspectral data and a pre-established wavelength extraction model, where the key wavelengths are related to the phosphorus content of the rubber tree leaves, and the pre-established wavelength extraction model is obtained by learning and training hyperspectral sample data and sample phosphorus content data pairs in a pre-established sample database by adopting a competitive adaptive reweighted sampling (CARS) algorithm and a successive projection algorithm (SPA); and inputting the key wavelengths into the pre-established phosphorus content prediction model to calculate the phosphorus content of the to-be-detected rubber tree leaves, where the pre-established phosphorus content prediction model is obtained by learning and training key sample wavelengths and the sample phosphorus content data by adopting a back-propagation neural network (BPNN) algorithm, and the key sample wavelengths are obtained by inputting the hyperspectral data in the sample database into the pre-established wavelength extraction model.

A computer readable storage medium storing a computer program is provided, where when the computer program is executed by a processor, the following steps are implemented:

acquiring hyperspectral data of to-be-detected rubber tree leaves;

extracting key wavelengths of the rubber tree leaves according to the hyperspectral data and a pre-established wavelength extraction model, where the key wavelengths are related to the phosphorus content of the rubber tree leaves, and the pre-established wavelength extraction model is obtained by learning and training hyperspectral sample data and sample phosphorus content data pairs in a pre-established sample database by adopting a competitive adaptive reweighted sampling (CARS) algorithm and a successive projection algorithm (SPA); and inputting the key wavelengths into the pre-established phosphorus content prediction model to calculate the phosphorus content of the to-be-detected rubber tree leaves, where the pre-established phosphorus content prediction model is obtained by learning and training key sample wavelengths and the sample phosphorus content data by adopting a back-propagation neural network (BPNN) algorithm, and the key sample wavelengths are obtained by inputting the hyperspectral data in the sample database into the pre-established wavelength extraction model.

According to the foregoing method, system, computer device, and storage medium, a pre-established wavelength extraction model is obtained by learning and training hyperspectral sample data and sample phosphorus content data in a sample database through a CARS algorithm and a SPA; and a pre-established phosphorus content prediction model is obtained by learning and training key sample wavelengths and sample phosphorus content data through a BPNN algorithm. Therefore, when a phosphorus content of to-be-detected rubber tree leaves needs to be detected, only hyperspectral data of the to-be-detected rubber tree leaves needs to be measured, key wavelengths can be obtained by inputting the hyperspectral data into the pre-established wavelength extraction model, and the phosphorus content of the to-be-detected rubber tree leaves can be obtained by inputting the key wavelengths into the pre-established phosphorus content prediction model. The method has simple operation process and can quickly measure the phosphorus content. Moreover, the CARS algorithm and the SPA are comprehensively applied to extract the key wavelengths closely related to the phosphorus content of the rubber tree leaves, thus greatly reducing the computation. In addition, the CARS algorithm can eliminate noise and irrelevant information in the hyperspectral data and improve the accuracy of model inversion.

DETAILED DESCRIPTION

To make the objectives, technical solutions, and advantages of the present application clearer, the following further describes the present application in detail with reference to the accompanying drawings and embodiments. It should be understood that the specific embodiments described herein are merely used to explain the present application, rather than to limit the present application.

Figure 1:
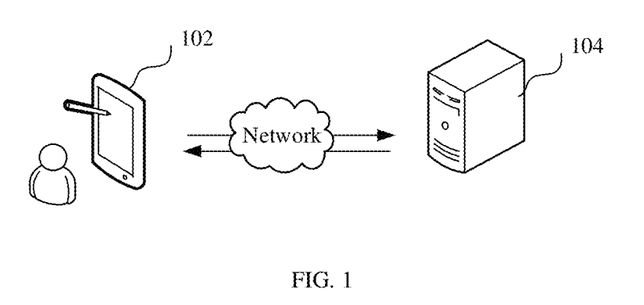
FIG. 1 is a schematic diagram of an application environment of a method for hyperspectral inversion of a phosphorus content of rubber tree leaves according to an embodiment.

The method is applied to a terminal 102 of FIG. 1, and the terminal may be a personal computer, a notebook computer, etc. The terminal 102 is in communication connection with a detection device 104, and the detection device 104 is usually a spectrometer, such as a FieldSpec3 spectrometer of ASD Company in the United States.

When the terminal 102 is connected to the detection device 104 by a local interface, the detection device 104 can send a collected to-be-identified video to the terminal 102. In addition, the terminal 102 can also acquire, through instructions, hyperspectral data of to-be-detected rubber tree leaves measured in the detection device 104.

Figure 2:
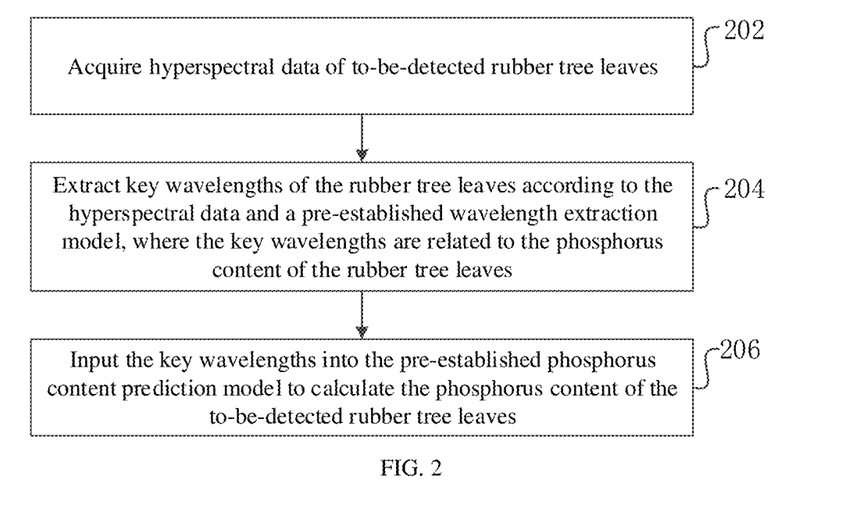
FIG. 2 is schematic flowchart of a method for hyperspectral inversion of a phosphorus content of rubber tree leaves according to an embodiment.

In an embodiment, as shown in FIG. 2, a method for hyperspectral inversion of a phosphorus content of rubber tree leaves is provided. Taking the application of the method to the terminal in FIG. 1 as an example for description, the method includes the following steps.

Step S202: Acquire hyperspectral data of to-be-detected rubber tree leaves.

The hyperspectral data is spectral data of the to-be-detected rubber tree leaves acquired by using a hyperspectral remote sensing technology. The hyperspectral remote sensing technology is a comprehensive detection technology based on modern physics, which uses an electromagnetic band to obtain relevant spectral data from an object under study. Hyperspectral remote sensing is to obtain a continuous spectral image of a ground object in a specific spectral region through high spectral resolution. Gray values of a first pixel point of the spectral image in each channel can form a fine spectral line, which finally forms a unique hyper-multidimensional spectral space. A sub-hyper-multidimensional spectral space can be used to study spatial information and obtain more spectral information, thus providing parameters and basis for quantitative analysis of physical and chemical changes of substances. At the same time, the hyperspectral remote sensing features high spectral resolution, large amount of spectral information, strong band continuity, etc. In addition, the to-be-detected rubber tree leaves are randomly collected according to certain tree leaf collection rules and methods from any rubber tree that needs to be subjected to phosphorus content detection.

Step S204: Extract key wavelengths of the rubber tree leaves according to the hyperspectral data and a pre-established wavelength extraction model, where the key wavelengths are related to the phosphorus content of the rubber tree leaves, and the pre-established wavelength extraction model is obtained by learning and training hyperspectral sample data and sample phosphorus content data pairs in a pre-established sample database by adopting a CARS algorithm and an SPA.

Specifically, researches show that the lack of certain nutrient elements (such as phosphorus or nitrogen) in a plant can cause changes in related biochemical components in the plant, which can cause differences in spectral reflectance at certain corresponding bands. These differences are shown as differences of color levels such as image saturation and image brightness on imaging spectral images. Therefore, a plant spectral curve is analyzed to extract sensitive spectral bands or feature bands with significant differences on the spectral curve, a corresponding nutrient estimation model is established by using mathematical statistics method, and a nutrient content of plants is retrieved. In this embodiment, the key wavelengths are sensitive bands or feature bands with significant difference in hyperspectral data of to-be-detected rubber tree leaves.

The CARS is a characteristic wavelength selection method based on Monte Carlo (MC) sampling and a PLS regression coefficient. That is, wavelength points with a large absolute value of the regression coefficient in a PLS model are selected through an adaptive reweighted sampling (ARS) technology, wavelength points with small weight are removed, and a subset with a lowest RMSECV value is selected through interactive verification, so that an optimal variable combination can be effectively found. The CARS algorithm can remove noise and irrelevant information from hyperspectral wavelengths, but the reserved wavelengths often have colinearity. The SPA can eliminate the colinearity between wavelengths.

The SPA is a forward variable selection algorithm that minimizes colinearity in vector space. Its advantage is that it extracts several characteristic wavelengths in the full band, can eliminate redundant information in an original spectral matrix and can be used for screening of spectral characteristic wavelengths.

The essence of model learning and training is a process of using one parameter as an X variable and the other parameter as a Y variable, and using a corresponding function to build a model. In this embodiment, hyperspectral sample data is used as the X variable, sample phosphorus content data is used as the Y variable, and a CARS algorithm and an SPA are used to establish a wavelength extraction model.

The pre-established sample database stores hyperspectral data and phosphorus content data of rubber tree leaves.

Step S206: Input the key wavelengths into the pre-established phosphorus content prediction model to calculate the phosphorus content of the to-be-detected rubber tree leaves, where the pre-established phosphorus content prediction model is obtained by learning and training key sample wavelengths and the sample phosphorus content data by adopting a BPNN algorithm, and the key sample wavelengths are obtained by inputting the hyperspectral data in the sample database into the pre-established wavelength extraction model.

A neural network is a non-linear system made up of a large number of simple computing units (namely neurons). The neural network includes an input layer, an output layer, and an intermediate layer between the input layer and the output layer. The basic idea of the neural network algorithm is as follows: A learning process consists of two processes: the forward propagation of a signal and the back propagation of an error. In the forward propagation, an input sample is processed layer by layer from the input layer through a hidden layer unit and transmitted to the output layer. In the process of layer-by-layer processing, a state of neurons in each layer only affects a state of neurons in the lower layer. If the output layer fails to obtain a desired output result, then it switches to the back propagation stage of the error. The output error is returned to the input layer layer by layer through a hidden layer through some form, and distributed to all units of each layer, thereby obtaining an error signal and a reference error of each layer unit, which can be used as a basis for modifying the weight of each unit. In this embodiment, the key sample wavelengths are used as network input layer parameters, and a sample phosphorus content parameter is used as a network output layer parameter, and a BPNN algorithm is learned and trained, thereby obtaining a phosphorus content prediction model.

According to the foregoing method for hyperspectral inversion of a phosphorus content of rubber tree leaves, a pre-established wavelength extraction model is obtained by learning and training hyperspectral sample data and sample phosphorus content data in a sample database through a CARS algorithm and an SPA; and a pre-established phosphorus content prediction model is obtained by learning and training key sample wavelengths and sample phosphorus content data through a BPNN algorithm. Therefore, when a phosphorus content of to-be-detected rubber tree leaves needs to be detected, only hyperspectral data of the to-be-detected rubber tree leaves needs to be measured, key wavelengths can be obtained by inputting the hyperspectral data into the pre-established wavelength extraction model, and the phosphorus content of the to-be-detected rubber tree leaves can be obtained by inputting the key wavelengths into the pre-established phosphorus content prediction model. The method has simple operation process and can quickly measure the phosphorus content. Moreover, the CARS algorithm and the SPA are comprehensively applied to extract the key wavelengths closely related to the phosphorus content of the rubber tree leaves, thus greatly reducing the computation. In addition, the CARS algorithm can eliminate noise and irrelevant information in the hyperspectral data and improve the accuracy of model inversion.

In an embodiment, before the step of acquiring hyperspectral data of to-be-detected rubber tree leaves, the method includes:

collecting to-be-detected rubber tree leaves;

performing spectral measurement on the to-be-detected rubber tree leaves by using a spectrometer tester to obtain original hyperspectral data of the to-be-detected rubber tree leaves; and denoising the original hyperspectral data to obtain hyperspectral data.

Specifically, in order to obtain hyperspectral data of the to-be-detected rubber tree leaves, the to-be-detected rubber tree leaves are collected first, and a plurality of rubber tree leaves can be randomly collected from a target rubber tree when the to-be-detected rubber tree leaves are collected. After the to-be-detected rubber tree leaves are collected, dust, impurities, etc. on the surfaces of the blades are removed, and then a spectrometer is used to measure the to-be-detected rubber tree leaves to obtain original hyperspectral data. In the process of obtaining the original hyperspectral data through measurement, multiple rubber leaves from the same target rubber tree are measured respectively to obtain multiple spectral data, and then the multiple spectral data is averaged, and the average is used as original hyperspectral data of the to-be-detected rubber tree leaves; and after being obtained, the original hyperspectral data is denoised, that is, the noise in the original hyperspectral data is processed to obtain the hyperspectral data. The original hyperspectral data obtained by the foregoing method is more accurate, and the original hyperspectral data is denoised to reduce noise interference, so that the finally obtained phosphorus content result is more accurate.

Figure 3:
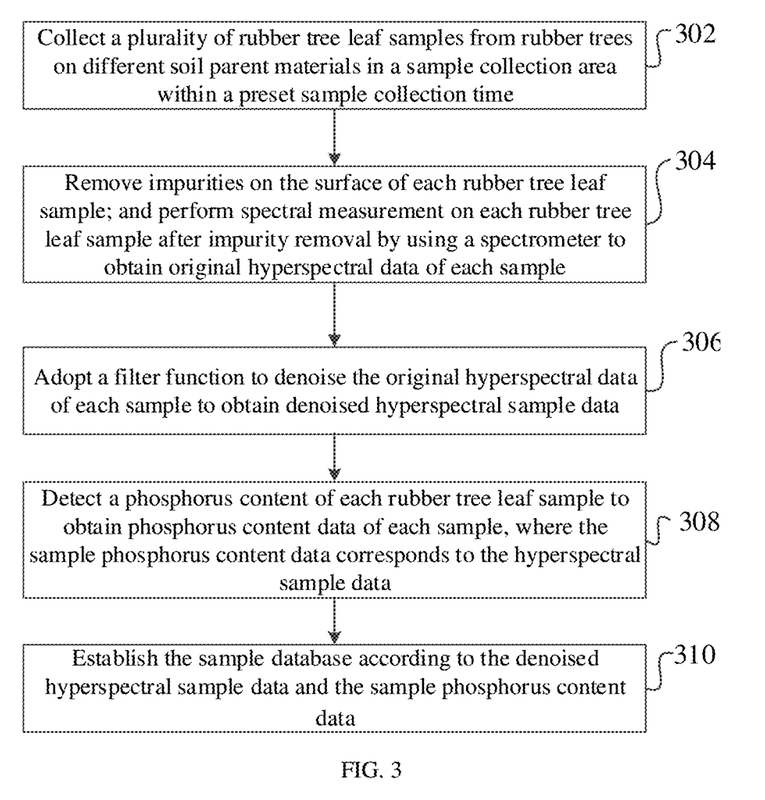
FIG. 3 is a schematic flowchart of a method for establishing a pre-established sample database in a method for hyperspectral inversion of a phosphorus content of rubber tree leaves according to an embodiment.

In an embodiment, as shown in FIG. 3, a method for establishing a pre-established sample database includes:

Step S302: Collect a plurality of rubber tree leaf samples from rubber trees on different soil parent materials in a sample collection area within a preset sample collection time.

The preset sample collection time is determined by comprehensively considering environmental factors such as plant growth cycle, light and climate. The sample collection area is usually determined according to the needs of researchers. For example, if researchers want to study a phosphorus content of rubber tree leaves of an area A, they can select the area A as the sample collection area. Different soil parent materials affect the growth of plants. Therefore, when rubber tree leaf samples are collected, the samples are taken from different soil parent materials to ensure the diversity and integrity of the samples. In this embodiment, Hainan Island is selected as the sample collection area.

Step S304: Remove impurities on the surface of each rubber tree leaf sample; and perform spectral measurement on each rubber tree leaf sample after impurity removal by using a spectrometer to obtain original hyperspectral data of each sample.

In order to reduce the influence of leaf surface impurities (such as dust) on a spectrometer, the impurities on the surfaces of the rubber tree leaf samples are removed.

Step S306: Adopt a filter function to denoise the original hyperspectral data of each sample to obtain denoised hyperspectral sample data.

Because the original hyperspectral data of each sample contains noise, the filter function is used to denoise the hyperspectral data of the sample. In an embodiment, the step of adopting a filter function to denoise the original hyperspectral data of each sample to obtain denoised hyperspectral sample data includes: adopting butter and filtfilt functions to denoise the original hyperspectral data of each sample.

Step S308: Detect a phosphorus content of each rubber tree leaf sample to obtain phosphorus content data of each sample, where the sample phosphorus content data corresponds to the hyperspectral sample data.

Step S310: Establish the sample database according to the denoised hyperspectral sample data and the sample phosphorus content data.

Figure 4:
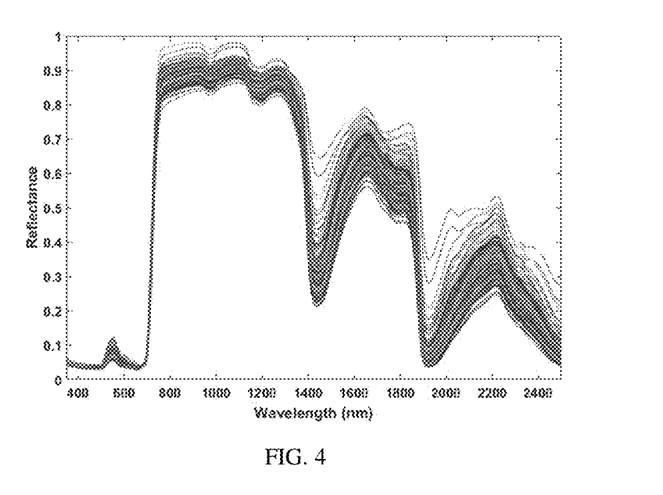
FIG. 4 is schematic diagram of hyperspectral data of a rubber tree leaf sample after denoising according to an embodiment.

In order to facilitate understanding of this solution, a detailed embodiment is given. A sample database establishment process is as follows: 1) Arrangement of sample collection points: Select nine rubber tree leaf sample collection points from four main soil parent materials (granite, basalt, metamorphic rock and sandshale) in Hainan Island. 2) Sample collection time: According to an annual change rule of rubber tree leaf nutrients, collect rubber tree leaf samples from the foregoing nine sample collection points from March to June (main leaf development stage), July to September (stable growth stage of rubber tree leaves) and October to December (aging stage of rubber tree leaves) each year. 3) Sample collection: When leaves are collected, cut stable canopy leaves on main lateral branches of a lower canopy layer of a rubber tree, and take the compound leaves on a base, where the leaves are required to be free of disease speckles. Take two leaves from each rubber tree, collect ten leaves from five rubber trees and mix the leaves as a leaf sample. 4) Pretreatment of fresh samples: After the leaves are collected, send the leaves to a laboratory quickly, wipe off dust on the surface of the leaves with a dry towel, and wait for spectral measurement. 5) Spectral measurement of the leaves: Measure the front spectrum of the rubber tree leaves by a FieldSpec3 spectrometer of ASD Company in the United States; during the measurement, connect a vegetation probe to the FieldSpec3 spectrometer, fix the leaves by leaf clips, and form, with the vegetation probe, a dark room provided with a light source. Select areas on both sides of the middle of a main vein of each blade for spectral collection, collect three spectra in the area of each side, and collect six spectra on both sides of each blade, and collect sixty spectra in total from each mixed sample. Average the sixty spectra, and take the average as the spectral value of the mixed sample. 6) Spectral processing: After the spectral measurement is completed, denoise the original spectrum by a filtering technology. Filtering is performed by using butter and filtfilt functions in Matlab software, where butter and filtfilt function models are as follows respectively: [B, A]=butter(N, Wn, 'low'), where N is the order of a filter; $W_n$ is a cut-off frequency of the filter; low stands for a low-pass filter; and B and A are filter coefficients of the butter function. Preferably, values of N and W are 2 and 0.5, respectively. spectrum=filtfilt(B, A, spectrum), where spectrum and spectrumF represent original hyperspectral data and denoised hyperspectral data respectively. See FIG. 4 for the denoised hyperspectral data. 7) Chemical measurement of a phosphorus content of the leaves: After the spectral measurement of the leaves is completed, place the leaf samples into an oven of 80° C. for sterilization for 20 min, then cool to 60° C., dry at constant temperature to a constant, and then grind the samples through a 0.25 mm sieve with a mortar; digest with concentrated $H_2SO_4$, make a measurement by using a Mo—Sb-Vc colorimetric method, and obtain a phosphorus content of the sample.

Figure 5:
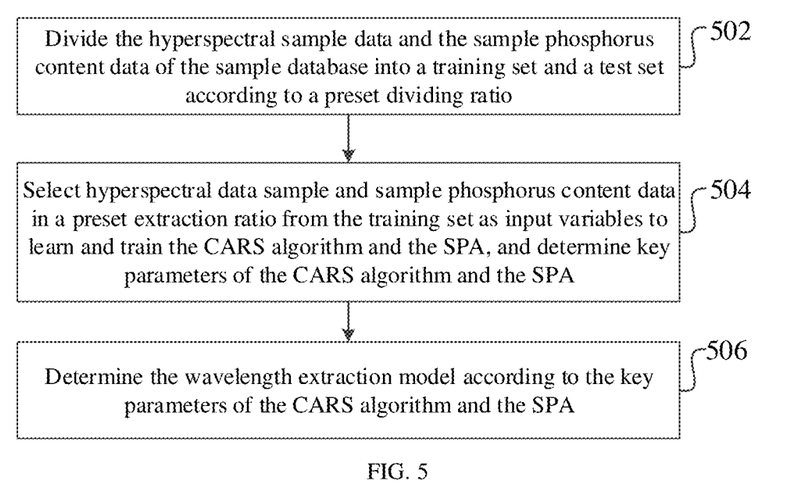
FIG. 5 is schematic flowchart of a method for hyperspectral inversion of a phosphorus content of rubber tree leaves according to another embodiment.

In an embodiment, as shown in FIG. 5, a method for establishing a pre-established wavelength extraction model includes:

Step S502: Divide the hyperspectral sample data and the sample phosphorus content data of the sample database into a training set and a test set according to a preset dividing ratio.

The preset dividing ratio can be preset according to actual requirements, but for the accuracy of model training, the training set usually has a greater sample number than the testing set. In an embodiment, the step of dividing the hyperspectral sample data and the sample phosphorus content data of the sample database into a training set and a test set according to a preset dividing ratio includes: adopting a Kennard-Stone algorithm to divide the hyperspectral sample data and the sample phosphorus content data of the sample database into a training set and a test set, where the ratio of the data volume of the training set to the data volume of the test set is 2:1. Descriptive statistical results of phosphorus contents in leaf samples of the training set and the test set are shown in Table 1. It can be seen that variation ranges, averages, standard deviations and coefficients of variation of the training set and the test set are very close, and the phosphorus contents in the leaves in the two sets also follow the normal distribution (−1<skewness<1).

TABLE 1

Statistics of phosphorus contents in rubber tree leaf samples

| Item | Range (%) | Mean (%) | SD (%) | CV (%) | Skewness |
|---|---|---|---|---|---|
| Train set (n = 288) | 0.156-0.460 | 0.270 | 0.058 | 21.481 | 0.769 |
| Test set (n = 143) | 0.154-0.434 | 0.264 | 0.057 | 21.591 | 0.657 |

Note:
SD is the standard deviation, CV is the coefficient of variation, and Skewness is the skewness of probability.

Step S504: Select hyperspectral data sample and sample phosphorus content data in a preset extraction ratio from the training set as input variables to learn and train the CARS algorithm and the SPA, and determine key parameters of the CARS algorithm and the SPA.

Step S506: Determine the wavelength extraction model according to the key parameters of the CARS algorithm and the SPA.

The essence of the model training is to determine the key parameters in the function. In this embodiment, the training processes of the CARS algorithm and the SPA are as follows: the CARS algorithm include the following main steps of: using an MC algorithm to select about 80% of samples from the training set for modeling; and selecting PLSR for modeling, where explanatory variables of the model are all spectral information (2151 wavelengths). The PLSR model is: y=Xb+e, where y is the phosphorus content $[y_1, y_2, y_3, \ldots, y_n]^T$ (T is transposition) of n rubber tree leaf samples, X is an n×p order spectral information matrix (p is the number of spectral wavelengths), b is a spectral wavelength coefficient $[b_1, b_2, b_3, \ldots, b_p]^T$, and e is an error term. After the PLSR model is established, the coefficient $b_p$ of each wavelength is recorded and an absolute value is taken. Then the weight $w_i$ of the absolute value of each wavelength coefficient is calculated, where $w_i=|b_i|/(|b_1|+|b_2|+|b_3|+ \ldots +|b_p|)$, i=1, 2, 3, . . . , p. Finally, the corresponding spectral wavelengths are sorted according to the order of weight from large to small; and an exponentially decreasing function (EDF) is used to eliminate spectral wavelength information with small weight. According to the EDF, the ratio $r_i$ of wavelengths needing to be reserved for each iteration operation is calculated. $r_i=ae^{-ki}$, where $r_i$ is the ratio of wavelengths needing to be reserved for the i-th iteration; a and k are two constant terms, calculation formulas are:

$a=(p/2)^{1/(N-1)}$ and $k=\ln(p/2)/(N-1)$ respectively, and N is the number of iterations. The number of spectral wavelengths reserved after each iteration is $p \times r_i$; an ARS algorithm is used to extract the wavelengths related to the phosphorus content of rubber tree leaves from $p \times r_i$ spectral wavelengths. The ARS algorithm selects wavelengths according to the principle of survival of the fittest in Darwin's evolution theory, that is, the greater the weight $w_i$ of which wavelength, the greater the chance of being selected; and the foregoing process is operated N times to obtain N groups of hyperspectral wavelengths. An RMSE of each group of hyperspectral wavelengths is calculated by a cross-validation (CV) method. The N groups of RMSEs are compared, and the group of hyperspectral wavelengths with the minimum RMSE is selected as a preferred variable.

Figure 6:
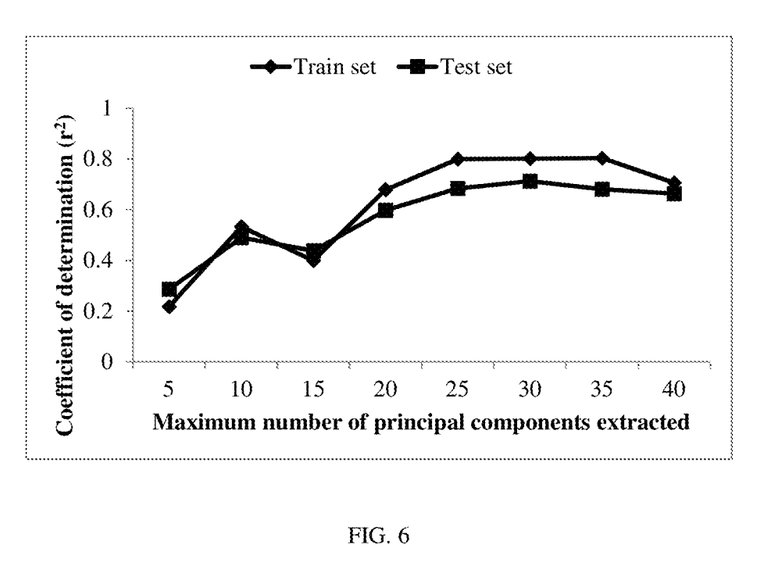
FIG. 6 is a schematic diagram of the maximum number of principal components extracted in PLSR and a coefficient of determination ($r^2$) of a corresponding model according to an embodiment.
Figure 7:
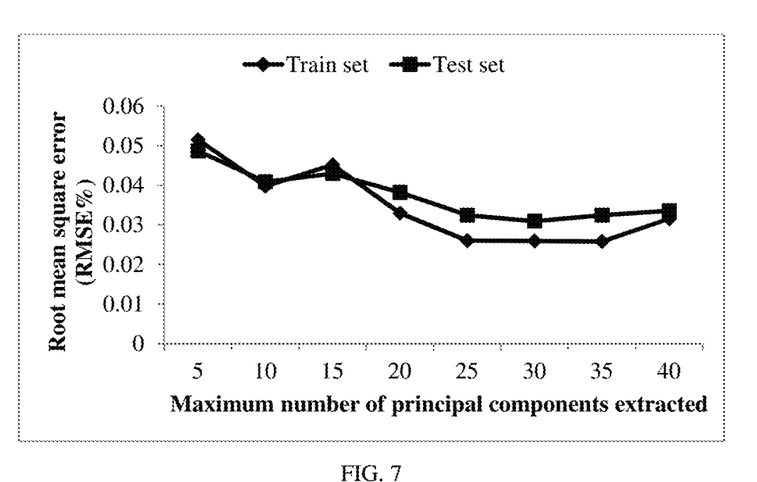
FIG. 7 is a schematic diagram of the maximum number of principal components extracted in PLSR and a RMSE of a corresponding model according to an embodiment.
Figure 8:
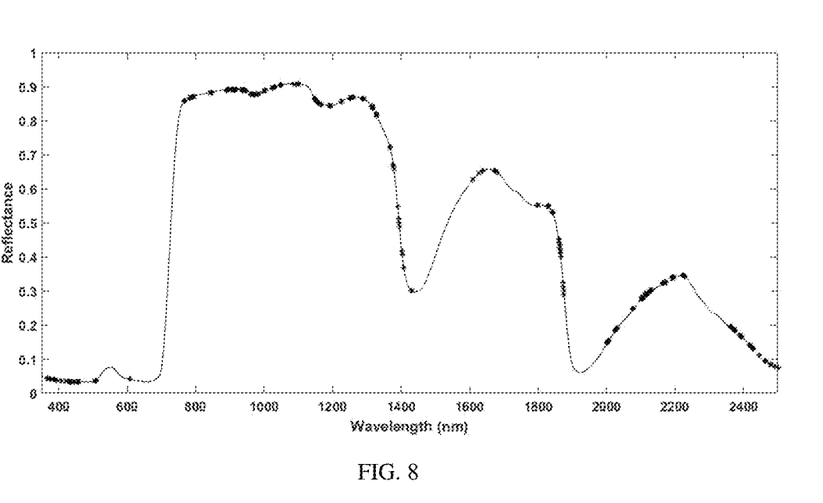
FIG. 8 is a schematic diagram of wavelengths extracted by a CARS algorithm and their positions in a full spectrum according to one embodiment.

When the CARS algorithm is running, the maximum number of principal components extracted from the PLSR model needs to be set first. This parameter can significantly affect variable selection. In order to find out optimal parameters, the parameters are set to 5, 10, 15, 20, 25, 30, 35 and 40 (namely the foregoing key parameters) respectively, the wavelengths obtained from each screening are used as explanatory variables to build the PLSR model, $r^2$ and the RMSE of the model in an independent verification set are calculated, and a group of wavelengths with the greatest $r^2$ and the minimum RMSE is selected as an object for further filtering. FIG. 6 shows change trends of the maximum number of principal components extracted from the PLSR model and $r^2$ of the corresponding model in the training set and the verification set. It can be seen that as the maximum number of extracted principal components changes from 5 to 30, $r^2$ in the training set and the verification set shows an overall upward trend, reaching the maximum value at 30 and then showing a downward trend. FIG. 7 shows change trends of the maximum number of principal components extracted from the PLSR model and the RMSE of the corresponding model in the training set and the verification set. It can also be seen that as the maximum number of extracted principal components changes from 5 to 30, the RMSEs in the training set and the verification set show an overall downward trend, reaching the lowest value at 30 and then showing an upward trend. Therefore, 30 is selected as the maximum number of principal components extracted in the PLSR model. Correspondingly, 293 wavelengths are selected. The positions of these wavelengths in the entire spectrum are shown in FIG. 8.

Figure 9:
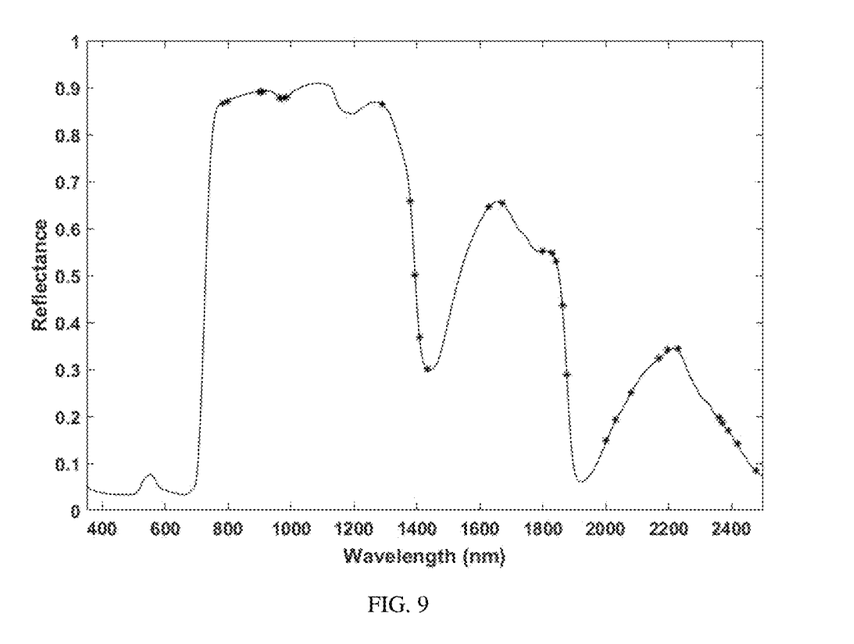
FIG. 9 is a schematic diagram of wavelengths extracted by an SPA and their positions in a full spectrum according to one embodiment.

When the CARS algorithm is completed, noise and irrelevant information from hyperspectral wavelengths can be removed, but the reserved wavelengths often have colinearity. The SPA can eliminate the colinearity between wavelengths. The SPA mainly includes the following steps. $X_{cal}$ is an $M_{cal} \times p$ order spectral wavelength information matrix of a training set, where $M_{cal}$ is the number of samples in the training set and p is the number of spectral wavelengths in the training set. A column vector $X_{cal(i)}$ is randomly extracted from the spectral wavelength information matrix $X_{cal}$ as an initial value (l=1, 2, 3, . . . , p), projection values of the remaining p−1 column vectors in the vertical plane of the column vector $X_{cal(i)}$ are calculated, and the column vector with the maximum projection value is selected. Next, the projection values of the remaining p−2 column vectors in the vertical plane of the column vector selected in step 1 are calculated, and the column vector with the maximum projection value is also selected. The process is repeated until $M_{cal-1}$ column vectors are selected and become a group of extracted spectral wavelength information, and the iteration is ended. Again, a column vector is randomly extracted from $X_{cal}$, and the foregoing process is repeated to obtain the second group of extracted spectral wavelength information, and the second iteration ends. Iteration continues until the p-th group of extracted spectral wavelength information is obtained. In the test set, the foregoing p groups of extracted spectral wavelength information are used as explanatory variables, a multiple linear regression (MLR) model is used to calculate RMSEs, and the group of spectral wavelength information with the minimum RMSE is selected as the preferred variable. The spectral wavelength information with the minimum RMSE selected in the previous step continues to be compressed. The specific steps are as follows: a relevance index (RI) of each piece of wavelength information is calculated first, where RI is the product of each wavelength coefficient and the standard deviation of the wavelength coefficient. The wavelengths are sorted according to the RI value, and RMSEs when the phosphorus content of rubber tree leaves is calculated by using the first k pieces of wavelength information (k≤the number of wavelength information in this group) are successively calculated, and the first k wavelengths with the minimum number of wavelengths, of which the RMSEs have no significant difference from the minimum RMSE in this group, are selected as the optimal variable set. The difference analysis of the RMSE is performed by adopting an F test, and the significance level α is set to 0.25. Finally, 31 wavelengths are selected as the key wavelengths, namely 781, 796, 897, 903, 911, 961, 969, 983, 1288, 1379, 1394, 1408, 1433, 1628, 1672, 1799, 1831, 1843, 1862, 1876, 2001, 2031, 2079, 2169, 2197, 2229, 2360, 2371, 2390, 2418, and 2478 nm, respectively. Their positions in the full spectrum are shown in FIG. 9.

In an embodiment, a method for establishing the pre-established phosphorus content prediction model includes:

inputting the hyperspectral sample data in the test set into the pre-established wavelength extraction model to obtain key wavelengths of the samples;

taking the key sample wavelengths and the sample phosphorus content data corresponding to the key sample wavelengths as input variables to learn and train the BPNN algorithm, and determining key parameters of the BPNN algorithm; and determining the phosphorus content prediction model according to the key parameters of the BPNN algorithm.

The learning and training process of the neural network algorithm includes the following steps of: in the training set, taking the 31 selected key wavelengths as input variables, and using a BPNN method to build the phosphorus content prediction model. A hyperspectral neural network inversion model consists of an input layer, hidden layers and an output layer. The process for building the phosphorus content prediction model takes the 31 key wavelengths as input layer parameters and the sample phosphorus content as an output layer parameter to determine the number of hidden layers, the number of neurons, a transfer function and training functions of the network (namely the key parameters of the BPNN algorithm). In this embodiment, the input layer of the phosphorus content prediction model includes 31 key wavelengths, the hidden layer has 5 neurons, and the output layer is the predicted value of the phosphorus content of rubber tree leaves.

After the phosphorus content prediction model is constructed, the phosphorus content prediction model is tested and verified; that is, the phosphorus content prediction model is verified by using the data in the test set. The predicted value of the inversion model is compared with the measured value of the leaf phosphorus content, and a model coefficient of determination $r^2$, an RMSE and a normalized root mean square error (NRMSE) are calculated. The closer $r^2$ is to 1, the closer RMSE and NRMSE are to 0, and the higher the prediction accuracy of the model.

Effect Embodiment

A conventional PLRS full spectrum model ($PLSR_{Full}$), a model combining PLSR with a CARS algorithm and the model of the present invention are respectively adopted to predict the phosphorus content of rubber tree leaves. Results are shown in Table 3. It can be seen that the prediction accuracy of the present invention is the highest in both the training set and the verification set, and is significantly superior to that of a conventional PLSR full spectrum model.

TABLE 3

Comparison of prediction accuracy of three models

| Model | Number of variables | Training set | | | Test set | | |
|---|---|---|---|---|---|---|---|
| | | $r^2$ | RMSE (%) | NRMSE (%) | $r^2$ | RMSE (%) | NRMSE (%) |
| $PLSR_{Full}$ | 2151 | 0.637 | 0.035 | 12.977 | 0.588 | 0.037 | 14.079 |
| $PLSR_{CARS}$ | 293 | 0.802 | 0.026 | 9.59 | 0.713 | 0.031 | 11.712 |
| $ANN_{CARS-SPA}$ | 31 | 0.826 | 0.025 | 9.16 | 0.791 | 0.026 | 9.991 |

It should be understood that although the steps in the flowcharts of FIGS. 2-3 and 5 are shown in sequence as indicated by arrows, these steps are not necessarily performed in sequence as indicated by arrows. Unless explicitly stated herein, the execution of these steps is not strictly limited in sequence, and these steps may be executed in other sequences. Moreover, at least some steps in FIGS. 2-3 and 5 may include a plurality of substeps or a plurality of stages, which are not necessarily executed at the same time, but may be executed at each time. The execution order of these substeps or stages is not necessarily sequential, and these substeps or stages may be executed alternately with other steps or at least some substeps or stages of other steps.

Figure 10:
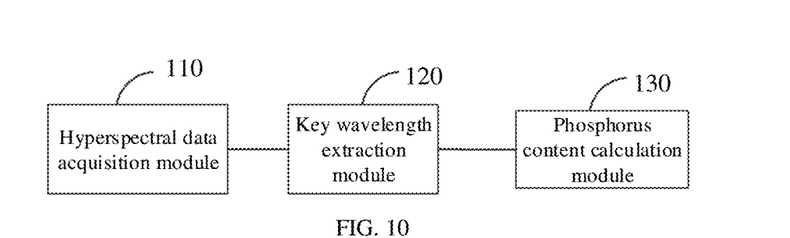
FIG. 10 is schematic structural diagram of a system for hyperspectral inversion of a phosphorus content of rubber tree leaves according to an embodiment.

In an embodiment, as shown in FIG. 10, a system for hyperspectral inversion of a phosphorus content of rubber tree leaves is provided, including:

a hyperspectral data acquisition module 110, configured to acquire hyperspectral data of to-be-detected rubber tree leaves;

a key wavelength extraction module 120, configured to extract key wavelengths of the rubber tree leaves according to the hyperspectral data and a pre-established wavelength extraction model, where the key wavelengths are related to the phosphorus content of the rubber tree leaves, and the pre-established wavelength extraction model is obtained by learning and training hyperspectral sample data and sample phosphorus content data pairs in a pre-established sample database by adopting a CARS algorithm and an SPA; and a phosphorus content calculation module 130, configured to input the key wavelengths into the pre-established phosphorus content prediction model to calculate the phosphorus content of the to-be-detected rubber tree leaves, where the pre-established phosphorus content prediction model is obtained by learning and training key sample wavelengths and the sample phosphorus content data by adopting a BPNN algorithm, and the key sample wavelengths are obtained by inputting the hyperspectral data in the sample database into the pre-established wavelength extraction model.

In an embodiment, the system further includes:

a leaf collection module, configured to collect to-be-detected rubber tree leaves;

a module for acquiring original hyperspectral data of blades, configured to perform spectral measurement on the to-be-detected rubber tree leaves by using a spectrometer tester to obtain original hyperspectral data of the to-be-detected rubber tree leaves; and a hyperspectral data acquisition module, configured to denoise the original hyperspectral data to obtain hyperspectral data.

In an embodiment, the system includes:

a sample collection module, configured to collect a plurality of rubber tree leaf samples from rubber trees on different soil parent materials in a sample collection area within a preset sample collection time;

a module for acquiring original hyperspectral data of samples, configured to remove impurities on the surface of each rubber tree leaf sample, and perform spectral measurement on each rubber tree leaf sample after impurity removal by using a spectrometer to obtain original hyperspectral data of each sample;

a hyperspectral sample data acquisition module, configured to adopt a filter function to denoise the original hyperspectral data of each sample to obtain denoised hyperspectral sample data;

a sample phosphorus content acquisition module, configured to detect a phosphorus content of each rubber tree leaf sample to obtain phosphorus content data of each sample, where the sample phosphorus content data corresponds to the hyperspectral sample data; and a sample database establishing module, configured to establish the sample database according to the denoised hyperspectral sample data and the corresponding sample phosphorus content data.

In an embodiment, the system includes:

a data set dividing module, configured to divide the hyperspectral sample data and the sample phosphorus content data of the sample database into a training set and a test set according to a preset dividing ratio;

a first key parameter determining module, configured to select hyperspectral data sample and sample phosphorus content data in a preset extraction ratio from the training set as input variables to learn and train the CARS algorithm and the SPA, and determine key parameters of the CARS algorithm and the SPA; and an extraction model determining module, configured to determine the wavelength extraction model according to the key parameters of the CARS algorithm and the SPA.

In an embodiment, the system includes:

a key wavelength acquisition module, configured to input the hyperspectral sample data in the test set into the pre-established wavelength extraction model to obtain key wavelengths of the samples;

a second key parameter determining module, configured to take the key sample wavelengths and the sample phosphorus content data corresponding to the key sample wavelengths as input variables to learn and train the BPNN algorithm, and determine key parameters of the BPNN algorithm; and a module for determining a phosphorus content prediction model, configured to determine the phosphorus content prediction model according to the key parameters of the BPNN algorithm.

In an embodiment, the hyperspectral sample data acquisition module is further configured to adopt butter and filtfilt functions to denoise the original hyperspectral data of each sample.

In an embodiment, the data set dividing module is further configured to adopt a Kennard-Stone algorithm to divide the hyperspectral sample data and the sample phosphorus content data of the sample database into a training set and a test set, where the ratio of the data volume of the training set to the data volume of the test set is 2:1.

For specific restrictions on a system for hyperspectral inversion of a phosphorus content of rubber tree leaves, a reference is made to the foregoing restrictions on the method for hyperspectral inversion of a phosphorus content of rubber tree leaves, which is not repeated herein. Various modules in the system for hyperspectral inversion of a phosphorus content of rubber tree leaves described above may be implemented fully or partially through software, hardware, and a combination thereof. Each of the foregoing modules may be embedded in or independent of a processor in a computer device in the form of hardware, or may be stored in a memory in the computer device in the form of software to enable the processor to conveniently call and execute operations corresponding to each of the foregoing modules.

Figure 11:
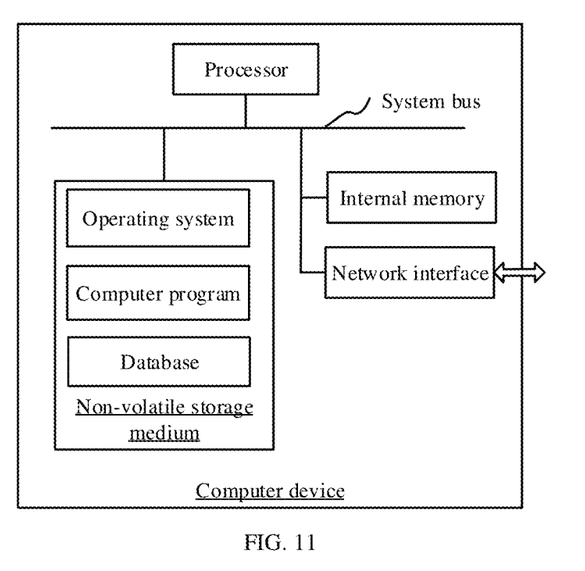
FIG. 11 is an internal structural diagram of a computer device according to an embodiment.

In an embodiment, a computer device is provided. The computer device may be a server, and an internal structure thereof may be as shown in FIG. 11. The computer device includes a processor, a memory, a network interface and a database which are connected through a system bus. The processor of the computer device is configured to provide computing and control capabilities. The memory of the computer device includes a non-volatile storage medium and an internal memory. The non-volatile storage medium stores an operating system, a computer program, and a database. The internal memory provides an environment for operations of the operating system and the computer program in the non-volatile storage medium. The database of the computer device is configured to store data of an equivalent resistance model and an equivalent submodel, as well as equivalent resistance, operating resistance and contact resistance obtained during calculation. The network interface of the computer device is configured to communicate with an external terminal through a network. When the computer program is executed by the processor, a method for hyperspectral inversion of a phosphorus content of rubber tree leaves is implemented.

Those skilled in the art may understand that the structure shown in FIG. 11 is only a block diagram of a part of the structure related to the solution of the present application and does not constitute a limitation on the computer device to which the solution of the present application is applied. The specific computer device may include more or fewer components than those shown in the figures, or combine some components, or have an arrangement of each component.

An embodiment provides a computer device, which includes a memory, a processor and a computer program stored on the memory and executable on the processor. When implementing the computer program, the processor implements the following steps of: acquiring hyperspectral data of to-be-detected rubber tree leaves; extracting key wavelengths of the rubber tree leaves according to the hyperspectral data and a pre-established wavelength extraction model, where the key wavelengths are related to the phosphorus content of the rubber tree leaves, and the pre-established wavelength extraction model is obtained by learning and training hyperspectral sample data and sample phosphorus content data pairs in a pre-established sample database by adopting a competitive self-adaptive reweigh sampling algorithm and a successive projection algorithm; and inputting the key wavelengths into a pre-established phosphorus content prediction model to calculate the phosphorus content of the to-be-detected rubber tree leaves, where the pre-established phosphorus content prediction model is obtained by learning and training key sample wavelengths and the sample phosphorus content data by adopting a back-propagation neural network algorithm, and the key sample wavelengths are obtained by inputting the hyperspectral data in the sample database into the pre-established wavelength extraction model.

In an embodiment, when implementing the computer program, the processor further implements the following steps including, before the step of acquiring hyperspectral data of to-be-detected rubber tree leaves, collecting to-be-detected rubber tree leaves; performing spectral measurement on the to-be-detected rubber tree leaves by using a spectrometer tester to obtain original hyperspectral data of the to-be-detected rubber tree leaves; and denoising the original hyperspectral data to obtain hyperspectral data.

In an embodiment, when implementing the computer program, the processor further implements the following steps: a method for establishing a pre-established sample database includes: collecting a plurality of rubber tree leaf samples from rubber trees on different soil parent materials in a sample collection area within a preset sample collection time; removing impurities on the surface of each rubber tree leaf sample; performing spectral measurement on each rubber tree leaf sample after impurity removal by using a spectrometer to obtain original hyperspectral data of each sample; adopting a filter function to denoise the original hyperspectral data of each sample to obtain denoised hyperspectral sample data; detecting a phosphorus content of each rubber tree leaf sample to obtain phosphorus content data of each sample, where the sample phosphorus content data corresponds to the hyperspectral sample data; and establishing the sample database according to the denoised hyperspectral sample data and the sample phosphorus content data.

In an embodiment, when implementing the computer program, the processor further implements the following steps: a method for establishing a pre-established wavelength extraction model includes: dividing the hyperspectral sample data and the sample phosphorus content data of the sample database into a training set and a test set according to a preset dividing ratio; selecting hyperspectral data sample and sample phosphorus content data in a preset extraction ratio from the training set as input variables to learn and train the CARS algorithm and the SPA, and determining key parameters of the CARS algorithm and the SPA; and determining the wavelength extraction model according to the key parameters of the CARS algorithm and the SPA.

In an embodiment, when implementing the computer program, the processor further implements the following steps: a method for establishing the pre-established phosphorus content prediction model includes: inputting the hyperspectral sample data in the test set into the pre-established wavelength extraction model to obtain key wavelengths of the samples; taking the key sample wavelengths and the sample phosphorus content data corresponding to the key sample wavelengths as input variables to learn and train the BPNN algorithm, and determining key parameters of the BPNN algorithm; and determining the phosphorus content prediction model according to the key parameters of the BPNN algorithm.

In an embodiment, when implementing the computer program, the processor further implements the following step: the step of adopting a filter function to denoise the original hyperspectral data of each sample to obtain denoised hyperspectral sample data includes: adopting butter and filtfilt functions to denoise the original hyperspectral data of each sample.

In an embodiment, when implementing the computer program, the processor further implements the following step: the step of dividing the hyperspectral sample data and the sample phosphorus content data of the sample database into a training set and a test set according to a preset dividing ratio includes: adopting a Kennard-Stone algorithm to divide the hyperspectral sample data and the sample phosphorus content data of the sample database into a training set and a test set, where the ratio of the data volume of the training set to the data volume of the test set is 2:1.

In an embodiment, a computer readable storage medium that stores a computer program is provided. When the computer program is executed by a processor, the following steps are implemented: acquiring hyperspectral data of to-be-detected rubber tree leaves; extracting key wavelengths of the rubber tree leaves according to the hyperspectral data and a pre-established wavelength extraction model, where the key wavelengths are related to the phosphorus content of the rubber tree leaves, and the pre-established wavelength extraction model is obtained by learning and training hyperspectral sample data and sample phosphorus content data pairs in a pre-established sample database by adopting a competitive adaptive reweighted sampling algorithm and a successive projection algorithm; and inputting the key wavelengths into a pre-established phosphorus content prediction model to calculate the phosphorus content of the to-be-detected rubber tree leaves, where the pre-established phosphorus content prediction model is obtained by learning and training key sample wavelengths and the sample phosphorus content data by adopting a BPNN algorithm, and the key sample wavelengths are obtained by inputting the hyperspectral data in the sample database into the pre-established wavelength extraction model.

In an embodiment, when the computer program is executed by the processor, the following steps are further implemented. Before the step of acquiring hyperspectral data of to-be-detected rubber tree leaves, the steps include collecting to-be-detected rubber tree leaves; performing spectral measurement on the to-be-detected rubber tree leaves by using a spectrometer tester to obtain original hyperspectral data of the to-be-detected rubber tree leaves; and denoising the original hyperspectral data to obtain hyperspectral data.

In an embodiment, when the computer program is implemented by the processor, the following steps are further implemented: a method for establishing a pre-established sample database includes: collecting a plurality of rubber tree leaf samples from rubber trees on different soil parent materials in a sample collection area within a preset sample collection time; removing impurities on the surface of each rubber tree leaf sample; performing spectral measurement on each rubber tree leaf sample after impurity removal by using a spectrometer to obtain original hyperspectral data of each sample; adopting a filter function to denoise the original hyperspectral data of each sample to obtain denoised hyperspectral sample data; detecting a phosphorus content of each rubber tree leaf sample to obtain phosphorus content data of each sample, where the sample phosphorus content data corresponds to the hyperspectral sample data; and establishing the sample database according to the denoised hyperspectral sample data and the sample phosphorus content data.

In an embodiment, when the computer program is implemented by the processor, the following steps are further implemented: a method for establishing a pre-established wavelength extraction model includes: dividing the hyperspectral sample data and the sample phosphorus content data of the sample database into a training set and a test set according to a preset dividing ratio; selecting hyperspectral data sample and sample phosphorus content data in a preset extraction ratio from the training set as input variables to learn and train the CARS algorithm and the SPA, and determining key parameters of the CARS algorithm and the SPA; and determining the wavelength extraction model according to the key parameters of the CARS algorithm and the SPA.

In an embodiment, when the computer program is implemented by the processor, the following steps are further implemented: a method for establishing the pre-established phosphorus content prediction model includes: inputting the hyperspectral sample data in the test set into the pre-established wavelength extraction model to obtain key wavelengths of the samples; taking the key sample wavelengths and the sample phosphorus content data corresponding to the key sample wavelengths as input variables to learn and train the BPNN algorithm, and determining key parameters of the BPNN algorithm; and determining the phosphorus content prediction model according to the key parameters of the BPNN algorithm.

In an embodiment, when the computer program is implemented by the processor, the following step is further implemented: the step of adopting a filter function to denoise the original hyperspectral data of each sample to obtain denoised hyperspectral sample data includes: adopting butter and filtfilt functions to denoise the original hyperspectral data of each sample.

In an embodiment, when the computer program is implemented by the processor, the following step is further implemented: the step of dividing the hyperspectral sample data and the sample phosphorus content data of the sample database into a training set and a test set according to a preset dividing ratio includes: adopting a Kennard-Stone algorithm to divide the hyperspectral sample data and the sample phosphorus content data of the sample database into a training set and a test set, where the ratio of the data volume of the training set to the data volume of the test set is 2:1.

Those of ordinary skill in the art can understand that all or some of processes for implementing the methods of the embodiments can be completed by instructing relevant hardware through a computer program. The computer program may be stored in a non-volatile computer readable storage medium. When the computer program is executed, processes of the embodiments of the methods may be included. For any reference used for a memory, a storage, a database, or other mediums used in various embodiments provided in this application may include a nonvolatile memory and/or a volatile memory. The non-volatile memory may include a read-only memory (ROM), a programmable ROM (PROM), an electrically programmable ROM (EPROM), an electrically erasable programmable ROM (EEPROM), or a flash memory. A volatile memory may include a random access memory (RAM) or an external cache memory. As description rather than limitation, the RAM can be obtained in a plurality of forms, such as a static RAM (SRAM), a dynamic RAM (DRAM), a synchronous DRAM (SDRAM), a double data rate SDRAM (DDRSDRAM), an enhanced SDRAM (ESDRAM), a Synchlink DRAM (SLDRAM), a Rambus direct RAM (RDRAM), a direct Rambus dynamic RAM (DRDRAM), and a Rambus dynamic RAM (RDRAM).

The technical features of the foregoing embodiments may be arbitrarily combined. For brevity of description, all possible combinations of the technical features in the embodiments are not described. However, as long as there is no contradiction between the combinations of these technical features, all these combinations should be considered as falling within the scope of this specification.

The foregoing embodiments are merely illustrative of several implementations of the present application, and the description thereof is more specific and detailed, but is not to be construed as a limitation to the claims of the present invention. It should be pointed out that several variations and improvements can be made by those of ordinary skill in the art without departing from the conception of the present application, and such variations and improvements should fall within the protection scope of the present application. Therefore, the protection scope of the present patent application should be subject to the appended claims.

What is claimed is:

1. A method for hyperspectral inversion of a phosphorus content of rubber tree leaves, comprising:
   acquiring hyperspectral data of to-be-detected rubber tree leaves;
   extracting key wavelengths of the rubber tree leaves according to the hyperspectral data and a pre-established wavelength extraction model, wherein the key wavelengths are related to the phosphorus content of the rubber tree leaves, and the pre-established wavelength extraction model is obtained by learning and training hyperspectral sample data and sample phosphorus content data pairs in a pre-established sample database by adopting a competitive adaptive reweighted sampling (CARS) algorithm and a successive projection algorithm (SPA); and
   inputting the key wavelengths into the pre-established phosphorus content prediction model to calculate the phosphorus content of the to-be-detected rubber tree leaves, wherein the pre-established phosphorus content prediction model is obtained by learning and training key sample wavelengths and the sample phosphorus content data by adopting a back-propagation neural network (BPNN) algorithm, and the key sample wavelengths are obtained by inputting the hyperspectral data in the sample database into the pre-established wavelength extraction model.

2. The method according to claim 1, wherein before the step of acquiring hyperspectral data of to-be-detected rubber tree leaves, the method comprises:
   collecting to-be-detected rubber tree leaves;
   performing spectral measurement on the to-be-detected rubber tree leaves by using a spectrometer tester to obtain original hyperspectral data of the to-be-detected rubber tree leaves; and
   denoising the original hyperspectral data to obtain hyperspectral data.

3. The method according to claim 1, wherein a method for establishing a pre-established sample database comprises:
   collecting a plurality of rubber tree leaf samples from rubber trees on different soil parent materials in a sample collection area within a preset sample collection time;
   removing impurities on the surface of each rubber tree leaf sample; performing spectral measurement on each rubber tree leaf sample after impurity removal by using a spectrometer to obtain original hyperspectral data of each sample;
   adopting a filter function to denoise the original hyperspectral data of each sample to obtain denoised hyperspectral sample data;
   detecting a phosphorus content of each rubber tree leaf sample to obtain phosphorus content data of each sample, wherein the sample phosphorus content data corresponds to the hyperspectral sample data; and
   establishing the sample database according to the denoised hyperspectral sample data and the sample phosphorus content data.

4. The method according to claim 1, wherein a method for establishing a pre-established wavelength extraction model comprises:
   dividing the hyperspectral sample data and the sample phosphorus content data of the sample database into a training set and a test set according to a preset dividing ratio;
   selecting hyperspectral data sample and sample phosphorus content data in a preset extraction ratio from the training set as input variables to learn and train the CARS algorithm and the SPA, and determining key parameters of the CARS algorithm and the SPA; and
   determining the wavelength extraction model according to the key parameters of the CARS algorithm and the SPA.

5. The method according to claim 2, wherein a method for establishing a pre-established wavelength extraction model comprises:
   dividing the hyperspectral sample data and the sample phosphorus content data of the sample database into a training set and a test set according to a preset dividing ratio;
   selecting hyperspectral data sample and sample phosphorus content data in a preset extraction ratio from the training set as input variables to learn and train the CARS algorithm and the SPA, and determining key parameters of the CARS algorithm and the SPA; and
   determining the wavelength extraction model according to the key parameters of the CARS algorithm and the SPA.

6. The method according to claim 3, wherein a method for establishing a pre-established wavelength extraction model comprises:
   dividing the hyperspectral sample data and the sample phosphorus content data of the sample database into a training set and a test set according to a preset dividing ratio;
   selecting hyperspectral data sample and sample phosphorus content data in a preset extraction ratio from the training set as input variables to learn and train the CARS algorithm and the SPA, and determining key parameters of the CARS algorithm and the SPA; and determining the wavelength extraction model according to the key parameters of the CARS algorithm and the SPA.

7. The method according to claim 4, wherein a method for establishing the pre-established phosphorus content prediction model comprises:

inputting the hyperspectral sample data in the test set into the pre-established wavelength extraction model to obtain key wavelengths of the samples;

taking the key sample wavelengths and the sample phosphorus content data corresponding to the key sample wavelengths as input variables to learn and train the BPNN algorithm, and determining key parameters of the BPNN algorithm; and determining the phosphorus content prediction model according to the key parameters of the BPNN algorithm.

8. The method according to claim 5, wherein a method for establishing the pre-established phosphorus content prediction model comprises:

inputting the hyperspectral sample data in the test set into the pre-established wavelength extraction model to obtain key wavelengths of the samples;

taking the key sample wavelengths and the sample phosphorus content data corresponding to the key sample wavelengths as input variables to learn and train the BPNN algorithm, and determining key parameters of the BPNN algorithm; and determining the phosphorus content prediction model according to the key parameters of the BPNN algorithm.

9. The method according to claim 6, wherein a method for establishing the pre-established phosphorus content prediction model comprises:

inputting the hyperspectral sample data in the test set into the pre-established wavelength extraction model to obtain key wavelengths of the samples;

taking the key sample wavelengths and the sample phosphorus content data corresponding to the key sample wavelengths as input variables to learn and train the BPNN algorithm, and determining key parameters of the BPNN algorithm; and determining the phosphorus content prediction model according to the key parameters of the BPNN algorithm.

10. The method according to claim 3, wherein the step of adopting a filter function to denoise the original hyperspectral data of each sample to obtain denoised hyperspectral sample data comprises:

adopting butter and filtfilt functions to denoise the original hyperspectral data of each sample.

11. The method according to claim 4, wherein the step of dividing the hyperspectral sample data and the sample phosphorus content data of the sample database into a training set and a test set according to a preset dividing ratio comprises:

adopting a Kennard-Stone algorithm to divide the hyperspectral sample data and the sample phosphorus content data of the sample database into a training set and a test set, wherein the ratio of the data volume of the training set to the data volume of the test set is 2:1.

12. The method according to claim 5, wherein the step of dividing the hyperspectral sample data and the sample phosphorus content data of the sample database into a training set and a test set according to a preset dividing ratio comprises:

adopting a Kennard-Stone algorithm to divide the hyperspectral sample data and the sample phosphorus content data of the sample database into a training set and a test set, wherein the ratio of the data volume of the training set to the data volume of the test set is 2:1.

13. The method according to claim 6, wherein the step of dividing the hyperspectral sample data and the sample phosphorus content data of the sample database into a training set and a test set according to a preset dividing ratio comprises:

adopting a Kennard-Stone algorithm to divide the hyperspectral sample data and the sample phosphorus content data of the sample database into a training set and a test set, wherein the ratio of the data volume of the training set to the data volume of the test set is 2:1.

14. A system for hyperspectral inversion of a phosphorus content of rubber tree leaves, comprising:

a hyperspectral data acquisition module, configured to acquire hyperspectral data of to-be-detected rubber tree leaves;

a key wavelength extraction module, configured to extract key wavelengths of the rubber tree leaves according to the hyperspectral data and a pre-established wavelength extraction model, wherein the key wavelengths are related to the phosphorus content of the rubber tree leaves, and the pre-established wavelength extraction model is obtained by learning and training hyperspectral sample data and sample phosphorus content data pairs in a pre-established sample database by adopting a competitive adaptive reweighted sampling (CARS) algorithm and a successive projection algorithm (SPA); and a phosphorus content calculation module, configured to input the key wavelengths into the pre-established phosphorus content prediction model to calculate the phosphorus content of the to-be-detected rubber tree leaves, wherein the pre-established phosphorus content prediction model is obtained by learning and training key sample wavelengths and the sample phosphorus content data by adopting a back-propagation neural network (BPNN) algorithm, and the key sample wavelengths are obtained by inputting the hyperspectral data in the sample database into the pre-established wavelength extraction model.

15. A computer device, comprising a memory, a processor, and a computer program stored in the memory and executable on the processor, wherein steps of any of the method according to claim 1 are implemented when the computer program is executed by the processor.

16. A computer device, comprising a memory, a processor, and a computer program stored in the memory and executable on the processor, wherein steps of any of the method according to claim 2 are implemented when the computer program is executed by the processor.

17. A computer device, comprising a memory, a processor, and a computer program stored in the memory and executable on the processor, wherein steps of any of the method according to claim 3 are implemented when the computer program is executed by the processor.

18. A computer device, comprising a memory, a processor, and a computer program stored in the memory and executable on the processor, wherein steps of any of the method according to claim 4 are implemented when the computer program is executed by the processor.

19. A computer readable storage medium storing a computer program, wherein steps of any of the method according to claim 1 are implemented when the computer program is executed by a processor.

20. A computer readable storage medium storing a computer program, wherein steps of any of the method according to claim 2 are implemented when the computer program is executed by a processor.

* * * * *